(12) United States Patent
Stevenson et al.

(10) Patent No.: US 9,382,201 B2
(45) Date of Patent: Jul. 5, 2016

(54) LIGHT-COLORED METAL WORKING ADDITIVES

(71) Applicant: Dover Chemical Corporation, Dover, OH (US)

(72) Inventors: Donald Stevenson, Dover, OH (US); John Nussbaumer, Bolivar, OH (US); Louis E. Bona, East Stroudsburg, PA (US)

(73) Assignee: Dover Chemical Corporation, Dover, OH (US)

( * ) Notice: Subject to any disclaimer, the term of this patent is extended or adjusted under 35 U.S.C. 154(b) by 0 days.

(21) Appl. No.: 14/283,942

(22) Filed: May 21, 2014

(65) Prior Publication Data
US 2014/0350290 A1  Nov. 27, 2014

Related U.S. Application Data

(60) Provisional application No. 61/825,750, filed on May 21, 2013.

(51) Int. Cl.
C07C 321/00 (2006.01)
C07C 323/12 (2006.01)
(52) U.S. Cl.
CPC .................................. *C07C 323/12* (2013.01)
(58) Field of Classification Search
CPC ............................. C07C 323/12; C07C 323/52
See application file for complete search history.

(56) References Cited

PUBLICATIONS

Jaschke et al. (Structure of Alkyl and Perfluoroalkyl Disulfide and Azobenzenethiol Monolayers on Gold(111) Revealed by Atomic Force Microscopy, J. Phys. Chem., 100, 2290-2301, 1996).*
Lubrizol 2007.*
*Morrison et al. (Morrison et al., Organic Chemistry fifth edition section 3.8, 1987).*
Koenig et al. (Reactivity of Acrylate-Terminated Au Nanoparticles: Suppressed Intramolecular Catalysis and Lack of Cooperative Effect Langmuir 2003, 19, 9511-9517).*

* cited by examiner

*Primary Examiner* — Yevegeny Valenrod
*Assistant Examiner* — Blaine G Doletski
(74) *Attorney, Agent, or Firm* — Black McCuskey Souers & Arbaugh, LPA

(57) ABSTRACT

A composition having a compound having the structure:

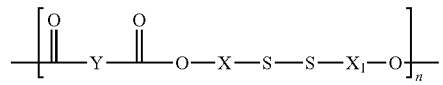

wherein n is an integer greater than or equal to 1;
wherein X is an alkyl moiety or aryl moiety;
wherein $X_1$ is an alkyl moiety or aryl moiety;
wherein Y is an alkyl moiety or aryl moiety, having a carbon number that is greater than or equal to 0, and
wherein if Y has a carbon number of 0, the compound has the structure:

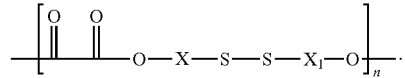

1 Claim, 1 Drawing Sheet

LIGHT-COLORED METAL WORKING ADDITIVES

CROSS REFERENCE TO RELATED APPLICATIONS

This utility patent application claims priority to U.S. provisional patent application Ser. No. 61/825,750, having a filing date of May 21, 2013. The provisional patent application's subject matter is hereby incorporated by reference into this application.

BACKGROUND OF THE INVENTION

Generally, "metalworking fluids" (MWF's) are oils and liquid-phase substances that are used during the machining of metal pieces in order to maintain their workability by cooling and lubricating them. MWFs reduce the heat and friction between the cutting tool and the workpiece while at the same time helping to prevent unwanted working conditions. MWF additives are added to a MWF in order to improve and enhance performance of the MWF.

There remains a need in the art for improved MWF's and MWF additives.

BRIEF SUMMARY OF THE INVENTION

A composition having a compound having the structure:

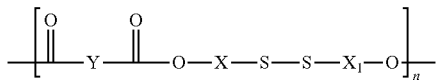

wherein n is an integer greater than or equal to 1;
wherein X is an alkyl moiety or aryl moiety;
wherein $X_1$ is an alkyl moiety or aryl moiety;
wherein Y is an alkyl moiety or aryl moiety, having a carbon number that is greater than or equal to 0; and
wherein if Y has a carbon number of 0, the compound has the structure:

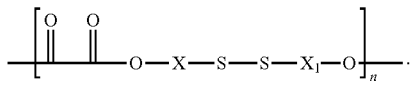

A method comprising the step of using a compound having the following structure, as a component in a metalworking fluid,:

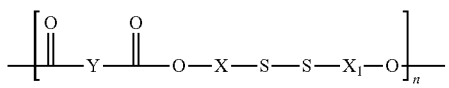

wherein n is an integer greater than or equal to 1;
wherein X is an alkyl moiety or aryl moiety;
wherein $X_1$ is an alkyl moiety or aryl moiety;
wherein Y is an alkyl moiety or aryl moiety having a carbon number that is greater than or equal to 0; and
wherein if Y has a carbon number of 0, the compound has the structure:

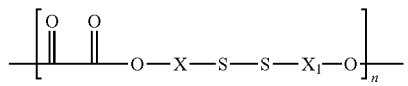

A composition having a compound having the structure:

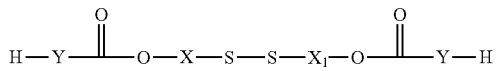

wherein X is an alkyl moiety or aryl moiety;
wherein $X_1$ is an alkyl moiety or aryl moiety;
wherein Y is an alkyl moiety or aryl moiety, having a carbon number that is greater than or equal to 0; and
wherein if Y has a carbon number of 0, the compound has the structure:

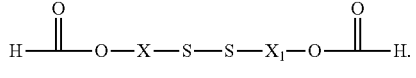

A method having the step of using a compound, having the following structure, as a component in a metalworking fluid:

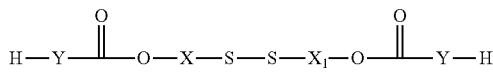

wherein X is an alkyl moiety or aryl moiety;
wherein $X_1$ is an alkyl moiety or aryl moiety;
wherein Y is an alkyl moiety or aryl moiety, having a carbon number that is greater than or equal to 0; and
wherein if Y has a carbon number of 0, the compound has the structure:

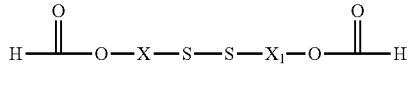

A composition having a compound having the structure:

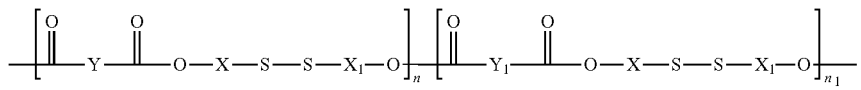

wherein n is an integer greater than or equal to 1;
wherein $n_1$ is an integer greater than or equal to 1;
wherein X is an alkyl moiety or aryl moiety;
wherein $X_1$ is an alkyl moiety or aryl moiety;
wherein Y is an alkyl moiety or aryl moiety, having a carbon number that is greater than or equal to 0;
wherein $Y_1$ is an alkyl moiety or aryl moiety, having a carbon number that is greater than or equal to 0; and
wherein if Y has a carbon number of 0, the compound has the structure:

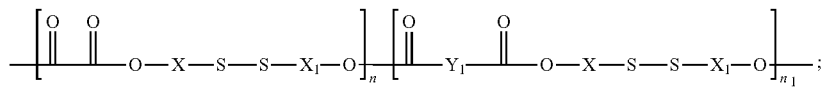

wherein if $Y_1$ has a carbon number of 0, the compound has the structure:

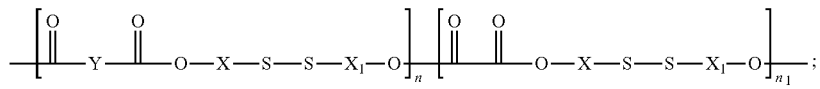

and
wherein Y has a different structure than $Y_1$.

A method having the step of using a compound, having the following structure, as a component in a metalworking fluid:

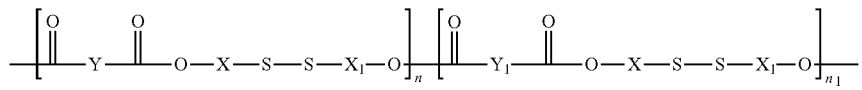

wherein n is an integer greater than or equal to 1;
wherein $n_1$ is an integer greater than or equal to 1;
wherein X is an alkyl moiety or aryl moiety;
wherein $X_1$ is an alkyl moiety or aryl moiety;
wherein Y is an alkyl moiety or aryl moiety, having a carbon number that is greater than or equal to 0;
wherein $Y_1$ is an alkyl moiety or aryl moiety, having a carbon number that is greater than or equal to 0; and
wherein if Y has a carbon number of 0, the compound has the structure:

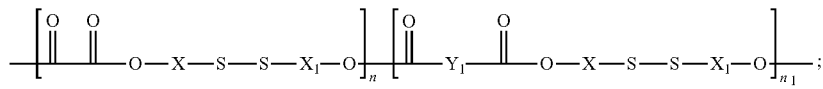

wherein if $Y_1$ has a carbon number of 0, the compound has the structure:

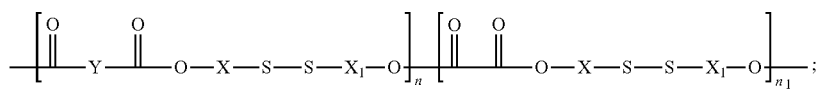

and
wherein Y has a different structure than $Y_1$.

A composition having a compound having the structure:

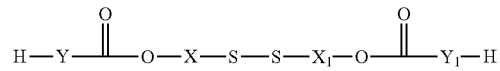

wherein X is an alkyl moiety or aryl moiety;
wherein $X_1$ is an alkyl moiety or aryl moiety;
wherein Y is an alkyl moiety or aryl moiety, having a carbon number that is greater than or equal to 0;
wherein $Y_1$ is an alkyl moiety or aryl moiety, having a carbon number that is greater than or equal to 0; and
wherein if Y has a carbon number of 0, the compound has the structure:

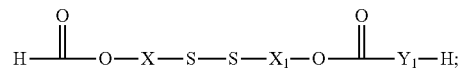

wherein if $Y_1$ has a carbon number of 0, the compound has the structure:

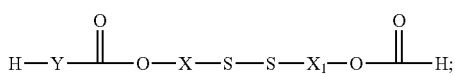

and wherein Y has a different structure than $Y_1$.

A method having the step of using a compound, having the following structure, as a component in a metalworking fluid:

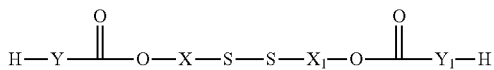

wherein X is an alkyl moiety or aryl moiety;
wherein $X_1$ is an alkyl moiety or aryl moiety;
wherein Y is an alkyl moiety or aryl moiety, having a carbon number that is greater than or equal to 0;

wherein $Y_1$ is an alkyl moiety or aryl moiety, having a carbon number that is greater than or equal to 0; and
wherein if Y has a carbon number of 0, the compound has the structure:

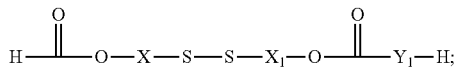

wherein if $Y_1$ has a carbon number of 0, the compound has the structure:

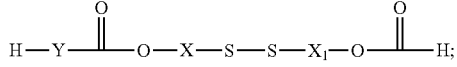

and wherein Y has a different structure than $Y_1$.

A composition having a compound having the structure:

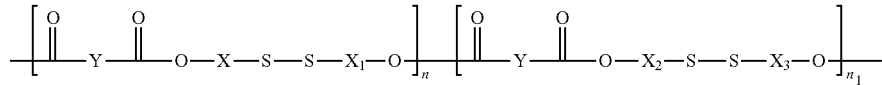

wherein n is an integer greater than or equal to 1;
wherein $n_1$ is an integer greater than or equal to 1;
wherein X is an alkyl moiety or aryl moiety;
wherein $X_1$ is an alkyl moiety or aryl moiety;
wherein $X_2$ is an alkyl moiety or aryl moiety;
wherein $X_3$ is an alkyl moiety or aryl moiety;
wherein Y is an alkyl moiety or aryl moiety, having a carbon number that is greater than or equal to 0; and
wherein if Y has a carbon number of 0, the compound has the structure:

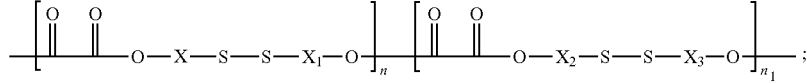

and
wherein

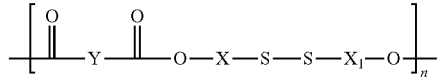

has a different structure than

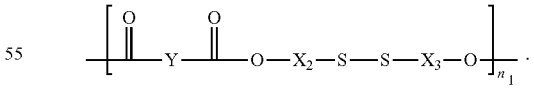

A method having the step of using a compound, having the following structure, as a component in a metalworking fluid:

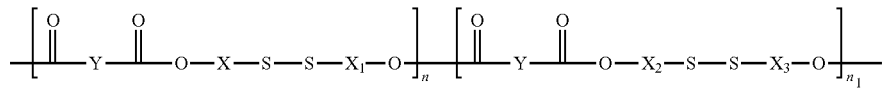

wherein n is an integer greater than or equal to 1;
wherein $n_1$ is an integer greater than or equal to 1;
wherein X is an alkyl moiety or aryl moiety;
wherein $X_1$ is an alkyl moiety or aryl moiety;
wherein $X_2$ is an alkyl moiety or aryl moiety;
wherein $X_3$ is an alkyl moiety or aryl moiety;
wherein Y is an alkyl moiety or aryl moiety, having a carbon number that is greater than or equal to 0; and
wherein if Y has a carbon number of 0, the compound has the structure:

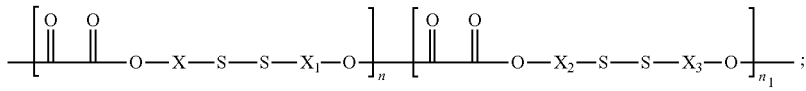

and
wherein

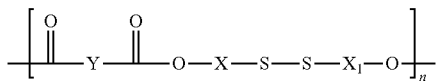

has a different structure than

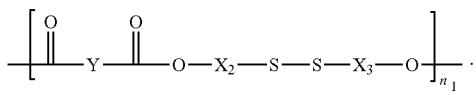

DETAILED DESCRIPTION OF THE INVENTION

Composition(s)

Figure 1:
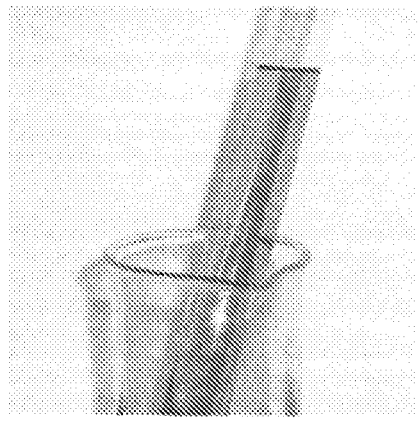
FIG. 1 shows the color of the New Additive.
Figure 2:
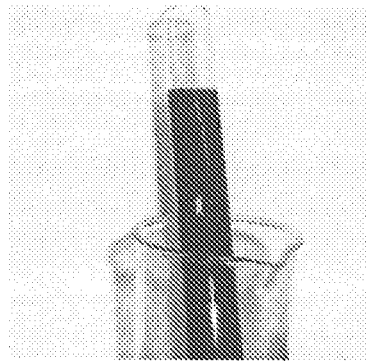
FIG. 2 shows the color of a Typical Sulfurized Ester.

The disclosed compositional embodiments are useful as MWF additives within a metalworking fluid (MWF).

I. An embodiment is directed to a composition that includes a compound having the structure:

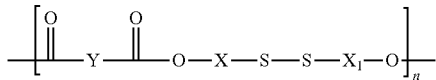

wherein n is an integer greater than or equal to 1;
wherein X is an alkyl moiety or aryl moiety;
wherein $X_1$ is an alkyl moiety or aryl moiety;
wherein Y is an alkyl moiety or aryl moiety, having a carbon number that is greater than or equal to 0; and
wherein if Y has a carbon number of 0, the compound has the structure:

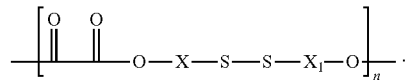

II. Another embodiment is directed to a composition that includes a compound having the structure:

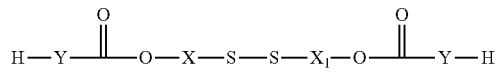

wherein X is an alkyl moiety or aryl moiety;
wherein $X_1$ is an alkyl moiety or aryl moiety;
wherein Y is an alkyl moiety or aryl moiety, having a carbon number that is greater than or equal to 0; and
wherein if Y has a carbon number of 0, the compound has the structure:

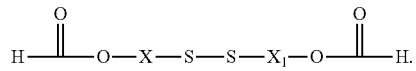

III. Another embodiment is directed to a composition that includes a compound having the structure:

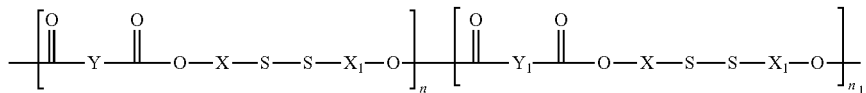

wherein n is an integer greater than or equal to 1;
wherein $n_1$ is an integer greater than or equal to 1;
wherein X is an alkyl moiety or aryl moiety;
wherein $X_1$ is an alkyl moiety or aryl moiety;
wherein Y is an alkyl moiety or aryl moiety, having a carbon number that is greater than or equal to 0;

wherein $Y_1$ is an alkyl moiety or aryl moiety, having a carbon number that is greater than or equal to 0; and wherein if Y has a carbon number of 0, the compound has the structure:

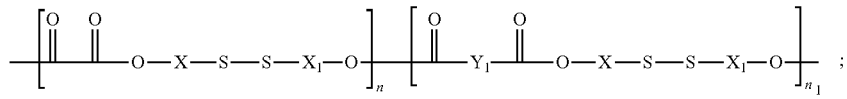

wherein if $Y_1$ has a carbon number of 0, the compound has the structure:

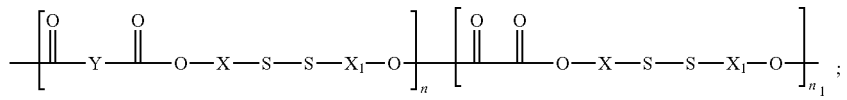

and wherein Y has a different structure than $Y_1$.

IV. Another embodiment is directed to a composition that includes a compound having the structure:

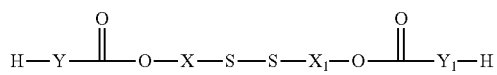

wherein X is an alkyl moiety or aryl moiety;

wherein $X_1$ is an alkyl moiety or aryl moiety;

wherein Y is an alkyl moiety or aryl moiety, having a carbon number that is greater than or equal to 0;

wherein $Y_1$ is an alkyl moiety or aryl moiety, having a carbon number that is greater than or equal to 0; and wherein if Y has a carbon number of 0, the compound has the structure:

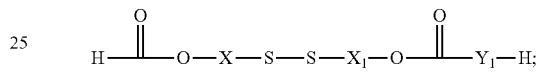

wherein if $Y_1$ has a carbon number of 0, the compound has the structure:

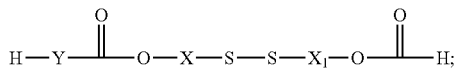

and wherein Y has a different structure than $Y_1$.

V. Another embodiment is directed to a composition that includes a compound having the structure:

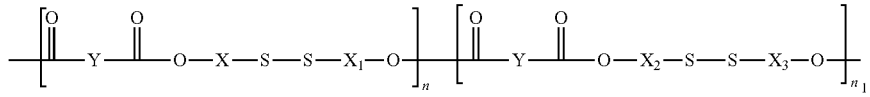

wherein n is an integer greater than or equal to 1;
wherein $n_1$ is an integer greater than or equal to 1;
wherein X is an alkyl moiety or aryl moiety;
wherein $X_1$ is an alkyl moiety or aryl moiety;
wherein $X_2$ is an alkyl moiety or aryl moiety;
wherein $X_3$ is an alkyl moiety or aryl moiety;
wherein Y is an alkyl moiety or aryl moiety, having a carbon number that is greater than or equal to 0; and
wherein if Y has a carbon number of 0, the compound has the structure:

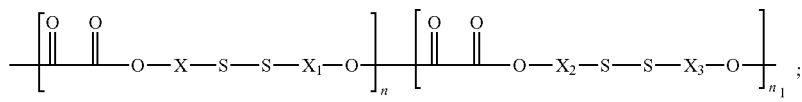

and
wherein

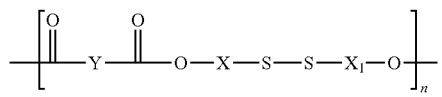

has a different structure than

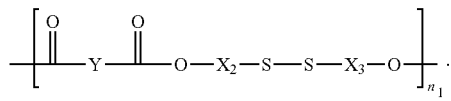

A chemical moiety can be understood as having its common definition(s). A simple non-limiting definition is that a moiety is a specific part of a compound.

An alkyl moiety can be understood as having its common definition(s). As a non-limiting definition, an alkyl moiety is a specific part of a compound consisting solely of single-bonded carbon and hydrogen atoms.

An aryl moiety can be understood as having its common definition(s). As a non-limiting definition, an aryl moiety is a specific part of a compound that includes an aromatic ring.

Carbon number is a term commonly used to describe the number of carbon atoms within a moiety or compound.

An integer is a whole number, i.e., a number without a fractional component.

Percent-by-weight can be understood as: [weight of the part]/[weight of the whole]×100%

In an embodiment, the sulfur content ranges from 2%-30% by weight; 5%-20% by weight, or 8%-15% by weight. In another embodiment, the sulfur content is less than 30.7%.

In the above embodiments, n can range from 1-100; $n_1$ can range from 1-100; Y can have a carbon number ranging from 0-36; $Y_1$ can have a carbon number ranging from 0-36; and X, $X_1$, $X_2$, or $X_3$ can have a carbon number ranging from 2-20.

Methods of Manufacture

Useful reactants for manufacturing the above-disclosed compounds include di-functional disulfides, mono-acids, di-acids, and combinations thereof; all of which are commercially available and readily accessible to a person of ordinary skill in the art. As a nonlimiting example, dihydroxy disulfides can be reacted with di-acids or mono-acids in order to arrive at one or more of the subject compounds. Useful di-functional disulfides include:

HO—X—S—S—$X_1$—OH wherein X is an alkyl moiety or aryl moiety; and
wherein $X_1$ is an alkyl moiety or aryl moiety.

Non-limiting examples of useful di-acids and mono-acids include:

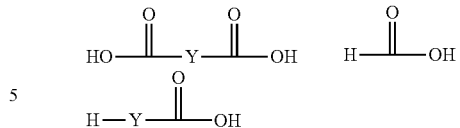

wherein Y is an alkyl moiety or aryl moiety, having a carbon number that is greater than or equal to 0.

Methods for manufacturing the subject compounds are provided:

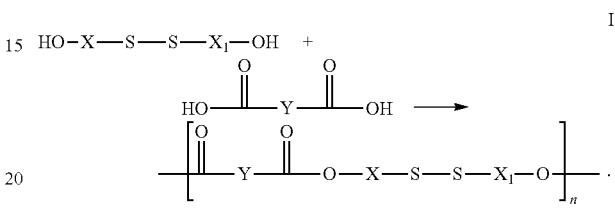

wherein n is an integer greater than or equal to 1;
wherein X is an alkyl moiety or aryl moiety;
wherein $X_1$ is an alkyl moiety or aryl moiety;
wherein Y is an alkyl moiety or aryl moiety, having a carbon number that is greater than or equal to 0; and
wherein if Y has a carbon number of 0, the yielded compound has the structure:

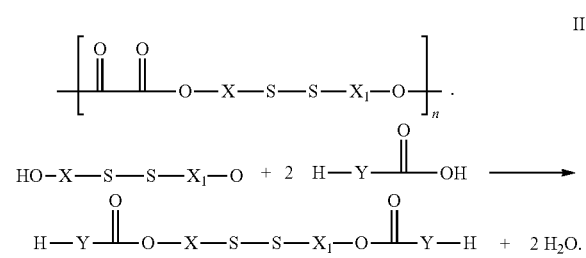

wherein X is an alkyl moiety or aryl moiety;
wherein $X_1$ is an alkyl moiety or aryl moiety;
wherein Y is an alkyl moiety or aryl moiety, having a carbon number that is greater than or equal to 0.

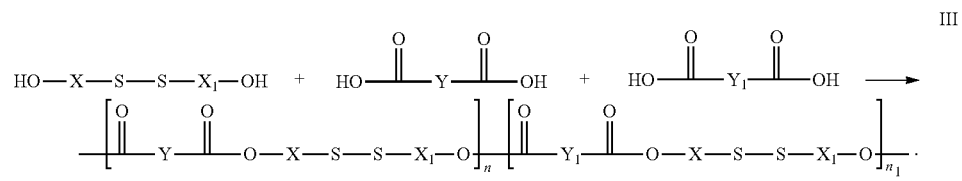

wherein n is an integer greater than or equal to 1;
wherein $n_1$ is an integer greater than or equal to 1;
wherein X is an alkyl moiety or aryl moiety;
wherein $X_1$ is an alkyl moiety or aryl moiety;
wherein Y is an alkyl moiety or aryl moiety, having a carbon number that is greater than or equal to 0;
wherein $Y_1$ is an alkyl moiety or aryl moiety, having a carbon number that is greater than or equal to 0; and
wherein if Y has a carbon number of 0, the yielded compound has the structure:

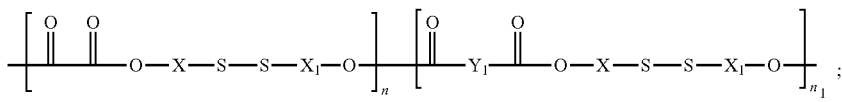

wherein if $Y_1$ has a carbon number of 0, the yielded compound has the structure:

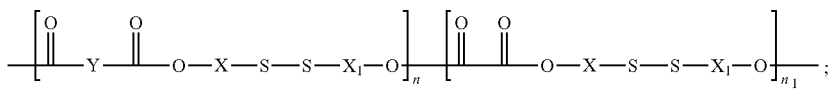

and
wherein Y has a different structure than $Y_1$.

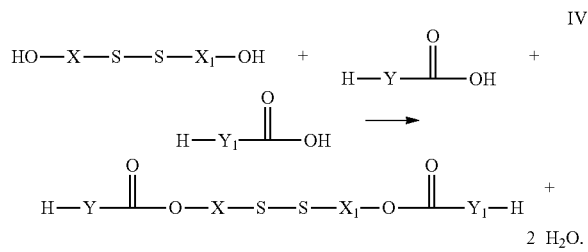

wherein X is an alkyl moiety or aryl moiety;
wherein $X_1$ is an alkyl moiety or aryl moiety;
wherein Y is an alkyl moiety or aryl moiety, having a carbon number that is greater than or equal to 0;
wherein $Y_1$ is an alkyl moiety or aryl moiety, having a carbon number that is greater than or equal to 0.

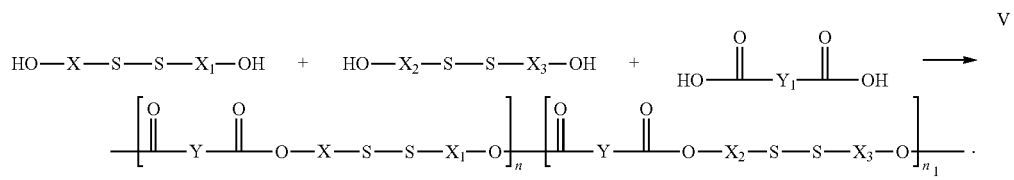

wherein n is an integer greater than or equal to 1;
wherein $n_1$ is an integer greater than or equal to 1;
wherein X is an alkyl moiety or aryl moiety;
wherein $X_1$ is an alkyl moiety or aryl moiety;
wherein $X_2$ is an alkyl moiety or aryl moiety;
wherein $X_3$ is an alkyl moiety or aryl moiety;
wherein Y is an alkyl moiety or aryl moiety, having a carbon number that is greater than or equal to 0.

Reaction Conditions

The above-described manufacturing reactions can be performed in the liquid phase, gas phase, or both by using well known chemical-reaction methods. In view of the below provided examples and descriptions, A person of ordinary skill in the art will be able to determine both useful amounts and reaction conditions without having to exercise undue experimentation.

Generally, manufacturing the above compounds can be performed at reaction temperatures ranging from: 165-170° C.; 140-185° C.; or 125-200° C.

Generally, manufacturing the above compounds can be done at ambient pressures or as described in the examples if one or more of the reactants is introduced via the gas phase.

Methods of Use

The disclosed embodiments are useful as MWF fluids or additives within a MWF.

The subject compounds are useful as a pure MWF or MWF additives in that can be determined by persons of ordinary skill in the art without having to exercise undue experimentation. As a non-limiting example, the additives can be used in amount equivalent to different MWF additives know in the art.

In embodiments, the subject MWF fluids or additives have a useful Gardner color range of less than 12 G. In another embodiment the subject MWF fluids or additives have a useful Gardner color ranging of less than 8 G.

EXAMPLES

1. To a three-neck 500 mL flask equipped with a magnetic stirrer and connected to a receiver was added 79.72 grams of Tall Oil Fatty Acid (0.283 mol), 20.53 grams of 2 Hydroxyethyl Disulfide (0.133 mol) and 0.35 grams of methane sulfonic acid. The mixture was mixed well and heat was applied to a reaction temperature of 165-170° C. This reaction takes place using a nitrogen blanket. The reaction was allowed to proceed until a final acid value of 10 or below was reached.

| | |
|---|---|
| Acid Value | 10 |
| Viscosity SUS 100F | >250 |
| Color, Gardner | Dark (>15G) |
| % Sulfur | 9.3 |

2. To a three-neck 500 mL flask equipped with a magnetic stirrer and connected to a receiver was added 21.85 grams (0.077 mol) of Oleic Acid, 20.00 grams (0.0355 mol) of Dimer Acid, 30.80 grams (0.214 mol) 2 Ethylhexanoic Acid and 27.00 grams (0.175 mol) 2 Hydroxyethyl Disulfide and 0.30 grams of Hypophosphorous Acid 50%. The mixture was mixed well and heat was applied to a reaction temperature of 165-170° C. This reaction takes place using a nitrogen blanket. The reaction was allowed to proceed until a final acid value of 10 or below was reached.

| | |
|---|---|
| Acid Value | 4.7 |
| Viscosity SUS 100F | 1050 |
| Color, Gardner | 10.7 |
| % Sulfur | 13 |

3. To a three-neck 500 mL flask equipped with a magnetic stirrer and connected to a receiver was added 53.74 grams (0.191 mol) Oleic Acid, 15.00 grams (0.027 mol) Dimer Acid, 29.76 grams (0.193 mol) of 2 Hydroxyethyl Disulfide and 0.30 grams of Dibutly Tin Oxide. The mixture was mixed well and heat was applied to a reaction temperature of 165-170° C. This reaction takes place using a nitrogen blanket. The reaction was allowed to proceed until a final acid value of 10 or below was reached.

| | |
|---|---|
| Acid Value | 8.3 |
| Viscosity SUS 100F | 247 |
| Color, Gardner | 13.5 |
| % Sulfur | 19 |

4. To a three-neck 500 mL flask equipped with a magnetic stirrer and connected to a receiver was added 14.35 grams (0.098 mol) Adipic Acid, 55.43 grams (0.197 mol) of Oleic Acid, 30.22 grams (0.196 mol) 2 Hydroxyethyl Disulfide and 0.30 grams of Dibutyl Tin Oxide. The mixture was mixed well and heat was applied to a reaction temperature of 165-17° C. This reaction takes place using a nitrogen blanket. The reaction was allowed to proceed until a final acid value of 10 or below was reached. This product is a paste at room temperature.

| | |
|---|---|
| Acid Value | 8.2 |
| Viscosity SUS 100F | Paste |
| Color, Gardner | 10.4 |
| % Sulfur | 19 |

5. To a three-neck 500 mL flask equipped with a magnetic stirrer and connected to a receiver was added 65.31 (0.232 mol) Oleic Acid, 34.69 grams (0.225 mol) 2 Hydroxyethyl Disulfide and 0.30 grams of Dibutyl Tin Oxide. The mixture was mixed well and heat was applied to a reaction temperature of 165-170° C. This reaction takes place using a nitrogen blanket. The reaction was allowed to proceed until a final acid value of 10 or below was reached.

| | |
|---|---|
| Acid Value | 5.9 |
| Viscosity SUS 100F | 192 |
| Color, Gardner | 6.6 |
| % Sulfur | 14.5 |

6. To a three-neck 500 mL flask equipped with a magnetic stirrer and connected to a receiver was added 43.82 grams (0.155 mol) 2 Oleic Acid, 26.18 grams (0.170 mol) 2 Hydroxyethyl Disulfide and 0.30 grams of Dibutyl Tin Oxide. The mixture was mixed well and heat was applied to a reaction temperature of 165-170° C. This reaction takes place using a nitrogen blanket. The reaction was allowed to proceed until a final acid value of 10 or below was reached. After acid value dropped below 10 mg/koh/g the product was allowed to cool. Once the temperature was <82° C. 30.00 grams (0.112 mol) Dodecyl Succinic Anhydride was added to the vessel.

| | |
|---|---|
| Acid Value | 0.7 |
| Viscosity SUS 100F | 392 |
| Color, Gardner | 7.2 |
| % Sulfur | 14.5 |

7. To a three-neck 500 mL flask equipped with a magnetic stirrer and connected to a receiver was added 51.18 grams (0.181 mol) Oleic Acid, 31.32 grams (0.203 mol) 2 Hydroxyethyl Disulfide and 0.30 grams Dibutyl Tin Oxide. The mixture was mixed well and heat was applied to a reaction temperature of 165-170° C. This reaction takes place using a nitrogen blanket. The reaction was allowed to proceed until a final acid value of 10 or below was reached. After acid value dropped below 10 mg/koh/g the product was allowed to cool. Once the temperature was <82° C. 17.50 grams (0.065 mol) Dodecyl Succinic Anhydride was added to the vessel.

| | |
|---|---|
| Acid Value | 12.4 |
| Viscosity SUS 100F | 163 |
| Color, Gardner | 6.9 |
| % Sulfur | 15.9 |

8. To a three-neck 500 mL flask equipped with a magnetic stirrer and connected to a receiver was added 71.69 grams (0.127 mol) Dimer Acid, 4.52 grams (0.031 mol) 2 Ethylhexanoic Acid, 23.79 grams (0.154 mol) 2 Hydroxyethyl Disulfide and 0.30 grams of Dibutyl Tin Oxide. The mixture was mixed well and heat was applied to a reaction temperature of 165-170° C. This reaction takes place using a nitrogen blanket. The reaction was allowed to proceed until a final acid value of 10 or below was reached. After acid value dropped below 1 mg/koh/g the product was allowed to cool.

| | |
|---|---|
| Acid Value | 7.5 |
| Viscosity SUS 100F | 167 |
| Color, Gardner | 7.2 |
| % Sulfur | 9.9 |

9. To a three-neck 500 mL flask equipped with a magnetic stirrer and connected to a receiver was added 78.55 grams (0.139 mol) Dimer Acid 21.45 grams (0.0.139 mol) 2 Hydroxyethyl Dislufide. The mixture was mixed well and heat was applied to a reaction temperature of 165-170° C. This reaction takes place using a nitrogen blanket. The reaction was allowed to proceed until a final acid value of 30 or below was reached. After acid value dropped below 30 mg/koh/g the product was allowed to cool.

| | |
|---|---|
| Acid Value | 30 |
| Viscosity SUS 100F | >1000 |
| Color, Gardner | 79 |
| % Sulfur | 9 |

10. To a three-neck flask equipped with a magnetic stirrer and connected to a receiver was added 69.61 grams (0.247 mol) Oleic Acid, 24.79 grams (0.161 mol) 2 Hydroxyethyl Disulfide. 5.30 grams (0.020 mol) Dodecylsuccinic Anhydride and 0.30 grams of Dibutyl Tin Oxide. The mixture was mixed well and heat was applied to a reaction temperature of 165-170° C. This reaction takes place using a nitrogen blanket. The reaction was allowed to proceed until a final acid value of 10 or below was reached. After acid value dropped below 10 mg/koh/g the product was allowed to cool. % Sulfur=10.4

| | | |
|---|---|---|
| | Acid Value | 10 |
| | Viscosity SUS 100F | 221 |
| | Color, Gardner | 7.9 |
| | % Sulfur | 10 |

11. To a three-neck flask equipped with a magnetic stirrer and connected to a receiver was added 40.87 grams (0.145 mol) Oleic Acid, 36.65 grams (0.238 mol) 2 Hydroxyethyl Disulfide, 22.18 grams (0.083 mol) Dodecylsuccinic Anhydride and 0.30 grams of Dibutyl Tin Oxide. The mixture was mixed well and heat was applied to a reaction temperature of 165-170° C. This reaction takes place using a nitrogen blanket. The reaction was allowed to proceed until a final acid value of 50 or below was reached. After acid value dropped below 50 mg/koh/g the product was allowed to cool. % Sulfur=15.9

| | | |
|---|---|---|
| | Acid Value | 48 |
| | Viscosity SUS 100F | 626 |
| | Color, Gardner | 7.9 |
| | % Sulfur | 15 |

Testing Methodology

Microtap Tap and Torque:

This test is typically used for testing cutting fluids. Testing involves the tapping of pre-drilled holes. Testing can be performed on aluminum, steel or stainless steel. The friction torque generated by tapping the holes is recorded in Newton centimeters (N-cm). Samples are compared to a standard, usually in this case Base 10SE a sulfurized vegetable ester. Microtap efficiencies were based on three runs for each sample. The standard's efficiency was set to 100%, with the other samples' efficiencies calculated against the standard. In all cases, higher tapping efficiencies mean better performing fluids. There is a +/−3% margin of error that is associated with the process.

| Parameter | Setting |
|---|---|
| Speed, rpm | 550 |
| Depth, mm | 15.0 |
| Material | Steel |
| Dilution Rate | 5% |

| Steel | Base 10SE | Example 5 | Example 6 | Example 7 | Example 8 |
|---|---|---|---|---|---|
| Avg. Ncm- | 210.6 | 207.1 | 206.1 | 203.8 | 201.0 |
| % Efficiency | 100.0 | 101.7 | 97.9 | 103.3 | 104.8 |

Four Ball Wear:

This test is used for evaluating friction-reducing and anti-wear fluids. Testing involves 3 stationary steel balls secured in a steel cup and a 4$^{th}$ steel ball lowered to make contact with the 3 stationary balls. The fluid to be tested is poured into the cup. The 4$^{th}$ ball is the only ball that spins. Typical rpm for the ball is 1200 rpm. The single ball spins in contact with the 3 stationary balls at a constant load of 40 kg. Typical run time is 1 hour. The wear on the lower 3 balls is measured and reported in mm. The fluid to produce the smallest wear scars has the best performance.

| Parameter | Setting |
|---|---|
| Load (kg) | 40 |
| Temperature | Ambient |
| Time (min) | 60 |
| Dilution Rate | 5% |
| Speed (rpm) | 1,200 |

| Ball | Base 10SE | Example 5 | Example 6 | Example 7 | Example 8 |
|---|---|---|---|---|---|
| 1 | 0.59 | 0.52 | 0.52 | 0.52 | 0.59 |
| 2 | 0.55 | 0.52 | 0.52 | 0.52 | 0.59 |
| 3 | 0.55 | 0.52 | 0.52 | 0.52 | 0.55 |
| Avg. mm | 0.56 | 0.52 | 0.52 | 0.52 | 0.57 |

Vertical Drawbead:

This test is used for evaluating drawing and forming fluids. Testing involves pulling an 18 in. long, 2 in. wide, and 0.032 in thick metal strip through a set of stationary dies. Testing can be performed on aluminum, steel or stainless steel. Drawbead strips were prepped for testing and then coated with the fluid to be evaluated. Results were based on two draws for each sample. Reported values are % efficiency (the efficiency of a fluid vs. the selected standard fluid). In all cases, lower % efficiency indicates less force required for the drawing operation and thus a better performing fluid. The selected standard's efficiency is set to 100.0%. Other samples efficiency values were subsequently measured against the standard. There is a +/−5% deviation associated with this process. For fluids with an efficiency that is worse than the standard (>5%), that sample efficiency will be labeled as a negative percent. Samples with a better efficiency rating than the standard will have a positive percent. All samples with an equivalent efficiency will be listed as 100%. The selected standard's efficiency was set to 100.0%.

| Parameter | Setting |
|---|---|
| Die Load (psi) | 500 |
| Die Temperature, F. | Ambient |
| Metal | Steel |
| Dilution Rate, % | 5% |
| Standard | 10% Sulfurized Ester |

| Sample | Efficiency, % |
|---|---|
| Base 10SE | 100.0 |
| Example 7 | +8.0 |

The invention claimed is:

1. A composition comprising:
a compound having the structure:

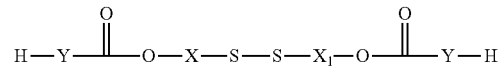

wherein X is an alkyl moiety or aryl moiety;
wherein $X_1$ is an alkyl moiety or aryl moiety;
wherein Y is an unsaturated alkyl moiety, having a carbon number that is 17; and
wherein X has a carbon number that is 2 or 20; and
wherein $X_1$ has a carbon number that is 2 or 20.

* * * * *